(12) United States Patent
Ser

(10) Patent No.: US 10,451,547 B2
(45) Date of Patent: *Oct. 22, 2019

(54) ILLUMINATION SYSTEM FOR RECOGNIZING MATERIAL AND METHOD OF RECOGNIZING MATERIAL USING THE SAME

(71) Applicant: DeeDiim Sensors Inc., Chuncheon-si, Gangwon-do (KR)

(72) Inventor: Jang-Il Ser, Chuncheon-si (KR)

(73) Assignee: DEEDIIM SENSORS INC., Chuncheon-si, Gangwon-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/229,356

(22) Filed: Dec. 21, 2018

(65) Prior Publication Data

US 2019/0120759 A1 Apr. 25, 2019

Related U.S. Application Data

(63) Continuation of application No. 15/430,916, filed on Feb. 13, 2017, now Pat. No. 10,161,865.

(30) Foreign Application Priority Data

Jul. 13, 2016 (KR) .................. 10-2016-0088759

(51) Int. Cl.
*G01N 21/47* (2006.01)
*G01N 21/55* (2014.01)

(52) U.S. Cl.
CPC ....... *G01N 21/4738* (2013.01); *G01N 21/474* (2013.01); *G01N 21/55* (2013.01);
(Continued)

(58) Field of Classification Search
CPC .. G01N 21/4738; G01N 21/474; G01N 21/55; G01N 2021/4716;
(Continued)

(56) References Cited

U.S. PATENT DOCUMENTS

| 4,917,495 | A | * | 4/1990 | Steenhoek | G01J 3/0251 356/328 |
| 5,166,985 | A | * | 11/1992 | Takagi | G01N 21/8806 348/128 |

(Continued)

FOREIGN PATENT DOCUMENTS

| JP | 2002-174595 | 6/2002 |
| JP | 2003-294622 | 10/2003 |
| JP | 2006-047290 | 2/2006 |

*Primary Examiner* — Sang H Nguyen
(74) *Attorney, Agent, or Firm* — Kile Park Reed & Houtteman PLLC

(57) ABSTRACT

An illumination system includes a measurement stage on which a measurement target is located, a light-providing part having illumination sections providing multi-directional incident lights to the measurement target, a light-receiving part receiving single-directional reflection lights reflected by the measurement target according to the multi-directional incident lights, and a processing part that performs acquiring a first distribution of intensities the single-directional reflection lights with respect to the multi-directional incident lights, acquiring, from the first distribution, a second distribution of intensities of multi-directional reflections lights with respect to a single-directional incident light, and determining material of the measurement target based on parameters of the second distribution. A method of recognizing material using the illumination system and a computer readable non-transitory recording medium recording a program embodying the method are provided.

14 Claims, 6 Drawing Sheets

(52) U.S. Cl.
CPC ........... *G01N 2021/4716* (2013.01); *G01N 2021/4733* (2013.01); *G01N 2021/556* (2013.01); *G01N 2201/0626* (2013.01); *G01N 2201/0634* (2013.01); *G01N 2201/0638* (2013.01); *G01N 2201/0655* (2013.01)

(58) Field of Classification Search
CPC ... G01N 2021/4733; G01N 2201/0634; G01N 2201/0638; G01N 2201/0655
See application file for complete search history.

(56) References Cited

U.S. PATENT DOCUMENTS

| | | | | |
|---|---|---|---|---|
| 5,245,671 A | * | 9/1993 | Kobayashi | G01N 21/8806 356/237.5 |
| 6,023,663 A | * | 2/2000 | Kim | G01N 21/95684 382/150 |
| 6,207,946 B1 | * | 3/2001 | Jusoh | G01N 21/8806 250/208.1 |
| 6,273,338 B1 | * | 8/2001 | White | G01N 21/8806 235/455 |
| 6,542,236 B1 | * | 4/2003 | Kim | G01N 21/8806 356/394 |
| 7,336,197 B2 | * | 2/2008 | Ding | G06K 7/10722 235/462.42 |
| 7,355,712 B2 | * | 4/2008 | Imura | G01N 21/4738 356/445 |
| 7,394,084 B2 | * | 7/2008 | Kuriyama | G01N 21/8806 250/559.34 |
| 7,505,149 B2 | * | 3/2009 | Ishiba | G01N 21/95684 356/237.1 |
| 7,667,856 B2 | * | 2/2010 | Fukamizu | G01J 3/02 356/601 |
| 7,872,753 B2 | * | 1/2011 | Frankinet | G01N 21/4738 250/458.1 |
| 2002/0196338 A1 | * | 12/2002 | Tham | G01N 21/8806 348/131 |
| 2008/0273193 A1 | * | 11/2008 | Nishiyama | G01N 21/9501 356/73 |
| 2017/0343482 A1 | * | 11/2017 | Kaupp | G01N 21/8806 |

\* cited by examiner

ILLUMINATION SYSTEM FOR RECOGNIZING MATERIAL AND METHOD OF RECOGNIZING MATERIAL USING THE SAME

CROSS REFERENCE TO RELATED APPLICATION

This application is a continuation application of U.S. patent application Ser. No. 15/430,916, filed Feb. 13, 2017 (now pending), the disclosure of which is herein incorporated by reference in its entirety. The U.S. patent application Ser. No. 15/430,916 claims priority to and the benefit of Korean Patent Applications No. 10-2016-0088759 filed Jul. 13, 2016, which is hereby incorporated by reference for all purposes as if fully set forth herein.

BACKGROUND OF THE INVENTION

Field of the Invention

Exemplary embodiments of the present invention relate to an illumination system for recognizing material and a method of recognizing material using the same. More particularly, exemplary embodiments of the present invention relate to an illumination system for recognizing material and a method of recognizing material using the same capable of recognizing material of an object.

Discussion of the Background

Generally, various methods of recognizing material of an object have been studied.

These methods typically employ a method of recognizing material of an object through an internal structure of the object, such as a method of analyzing material of the object by irradiating the object with an incident wave and measuring a reflected wave coming back.

However, since this method needs to grasp the internal structure of the object, this method complicates a system for material determination, greatly increases the manufacturing cost thereof. In addition, this method is not only difficult to determine material, but there is a limit to the determination of materials for various objects, and there is a problem that it is difficult to secure reliability.

Therefore, it is required to develop an illumination system for recognizing material and a method of recognizing material capable of easily and accurately recognize material of an object at a low cost.

SUMMARY OF THE INVENTION

Exemplary embodiments of the present invention provide an illumination system for recognizing material capable of easily and accurately recognizing material of an object at a low cost.

Exemplary embodiments of the present invention also provide a method of recognizing material using the illumination system for recognizing material.

Additional features of the invention will be set forth in the description which follows, and in part will be apparent from the description, or may be learned by practice of the invention.

In an exemplary embodiment of the present invention, an illumination system for recognizing material includes a measurement stage, a light-providing part, a light-receiving part, and a processing part. The measurement stage is upwardly open and on which a measurement target is located. The light-providing part includes a plurality of illumination sections providing multi-directional incident lights to the measurement target. The multi-directional incident lights have incident directions of incident angles, respectively. The light-receiving part receives single-directional reflection lights reflected by the measurement target according to the multi-directional incident lights provided by the light-providing part. The processing part performs steps of acquiring a first distribution of intensities the single-directional reflection lights with respect to the multi-directional incident lights; acquiring, from the first distribution, a second distribution of intensities of multi-directional reflections lights with respect to a single-directional incident light, wherein the multi-directional reflection lights of the second distribution have optical paths opposite to optical paths of the multi-directional incident lights of the first distribution, and the single-directional incident light of the second distribution has an optical path opposite to an optical path of the single-directional reflection lights of the first distribution; and determining material of the measurement target based on parameters of the second distribution.

In one embodiment, the light-providing part may include a plurality of first illumination sections covering at least a portion of multiple upper directions at which the measurement stage is open. The first illumination sections may form at least a portion of a dome shape.

In another embodiment, the light-providing part may include a plurality of first illumination sections covering at least a portion of multiple upper directions at which the measurement stage is open. The first illumination sections may form at least a portion of a plate shape. The multi-directional incident lights generated from the first illumination sections are provided at a point on the measurement target, the point meets an optical axis of the light-receiving part, and sizes of the first illumination sections may vary in such a manner that sections closer to a center of the measurement target are smaller than sections farther from the center of the measurement target so that solid angles of the incident lights covered by the first illumination sections are uniform.

In still another embodiment, the light-providing part may further include a refractive medium unit disposed below the first illumination sections to refract light generated from the first illumination sections so as to have a larger incident angle with respect to the measurement target.

In one embodiment, a first opening portion may be formed through a shape of the first illumination sections. The light-receiving part may be arranged so as to receive the reflection light reflected by the measurement target through the first opening portion. In one embodiment, the light-providing part may further include at least one second illumination section that provides incident light to the measurement target through the first opening portion, and may be configured to acquire the reflection light corresponding to a region of interest (ROI) including at least a portion of the measurement target.

For example, the at least one second illumination section may be formed as a plurality of layers forming at least a portion of a plate shape.

In one embodiment, a second opening portion may be formed through a shape of the at least one second illumination section. The light-receiving part may be arranged so as to receive the reflection light reflected by the measurement target through the second opening portion.

In one embodiment, the light providing part may further include a subsidiary illumination section providing incident light to the measurement target through the first opening portion, and a beam splitting unit that transmits the reflection lights to the light-receiving part and reflects the incident light generated from the subsidiary illumination section to provide the measurement target with the reflected incident light as an optical axis substantially the same as an optical axis of the light-receiving part.

For example, each of the first illumination sections may include a base substrate, a plurality of light sources formed on the base substrate, and a diffuser disposed in front of the light sources to diffuse light generated from the light sources.

In one embodiment, the light-receiving part may receive the single-directional reflection lights vertically and upwardly reflected from the measurement target, and the single-directional reflection lights are uniformly received with respect to illumination directions of the incident lights.

In one embodiment, the parameters may be acquired from a first intensity distribution of specular reflection lights and a second intensity distribution of diffuse reflection lights, the first and second intensity distributions forming the second distribution.

In one embodiment, the parameters include at least one of an area of the first intensity distribution, an area of the second intensity distribution, a total area of the first and second intensity distributions, a reflection angle of the first intensity distribution, and a spreading angle of the first intensity distribution.

For example, a value of each of the parameters may be obtained on a coordinate system between reflection angle and reflection intensity.

In one embodiment, the illumination system may further include a posture adjusting unit adjusting posture of the measurement target so as to maintain the posture of the measurement target constant with respect to incident directions of the multi-directional incident lights provided to the measurement target.

In an exemplary embodiment of the present invention, a method of recognizing material using an illumination system is provided. The method includes providing, by a light-providing device, multi-directional incident lights toward a measurement target, the multi-directional incident lights having incident directions of incident angles, respectively; receiving, by a light-receiving device, single-directional reflection lights reflected from the measurement target; acquiring, by a processor, a first distribution of intensities of the single-directional reflection lights with respect to the multi-directional incident lights; and acquiring from the first distribution, by the processor, a second distribution of intensities of the multi-directional reflection lights with respect to a single-directional incident light, wherein the multi-directional reflection lights of the second distribution have optical paths opposite to optical paths of the multi-directional incident lights of the first distribution, and the single-directional incident light of the second distribution has an optical path opposite to an optical path of the single-directional reflection lights of the first distribution; and determining, by the processor, material of the measurement target based on parameters of the second distribution.

In one embodiment, the parameters may be acquired from a first intensity distribution of specular reflection lights and a second intensity distribution of diffuse reflection lights, the first and second intensity distributions form the second distribution, and the parameters may include at least one of an area of the first intensity distribution, an area of the second intensity distribution, a total area of the first and second intensity distributions, a reflection angle of the first intensity distribution, and a spreading angle of the first intensity distribution.

In an exemplary embodiment of the present invention, a computer readable non-transitory recording medium recording a program embodying the above methods.

According to the present invention, multi-directional incident lights from a plurality of directions are provided to a measurement target, to obtain reflection lights in a single direction, from which thereafter a multi-directional intensity distribution of the reflection lights of the measurement target according to a single-directional incident light is acquired, to determine the material of the measurement target from the multi-directional intensity distribution of the reflection lights, thereby easily and accurately recognizing the material of the measurement target at a low cost in comparison with conventional systems.

In addition, when analyzing the intensity distribution of the reflected light into an intensity distribution of specular reflection light and an intensity distribution of the diffuse reflection light, and utilizing various parameters such as area, reflection angle, spread angle, etc. of the intensity distributions, more precise determination of the material may be available.

Further, when the illuminations are constituted by a dome shape, a plate shape, or the like, the reflected lights in a single direction according to the multi-directional incident lights may be obtained very conveniently and accurately.

In addition, when an opening is formed in correspondence to the light receiving-part that receives the reflected lights in the dome shape or the plate shape, the system may be realized much more compactly in comparison with a distance to be secured in order to obtain an image of a predetermined region of interest in the light-receiving part, and additional illuminations may be employed to compensate for partial absence of multi-directional incident lights due to the opening.

In addition, an additional illumination that is provided on the same optical axis as that of the light-receiving part may be employed, to thereby secure incident light in a direction of the optical axis of the light-receiving part.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
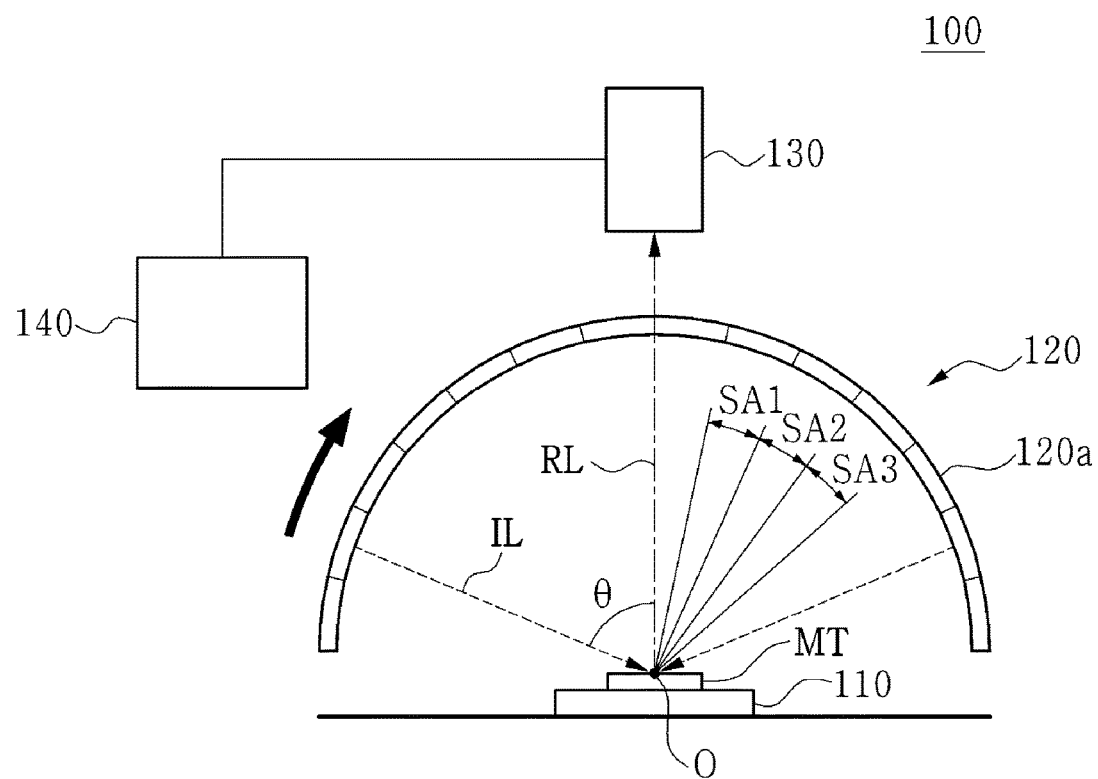
FIG. 1 is a conceptual view illustrating an illumination system for recognizing material according to an exemplary embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention may be illustrated as being implemented in a suitable computing environment. In addition, various methods according to the present invention may be provided as a recording medium that records a computer-software for implementing the methods.

The recording medium typically includes a variety of computer readable media, and may be provided as any available media that can be accessed by a computer. Further, the recording medium includes volatile or non-volatile media, removable or non-removable media, etc. For example, the recording medium may include all the media implemented in any method or technology for storage of information such as computer readable instructions, data structures, program modules or other data. In addition, the recording medium includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer.

Hereinafter, exemplary embodiments of the present invention will be described in detail with reference to the accompanying drawings.

FIG. 1 is a conceptual view illustrating an illumination system for recognizing material according to an exemplary embodiment of the present invention.

Referring to FIG. 1, an illumination system 100 for recognizing material according to an exemplary embodiment of the present invention includes a measurement stage 110, a light-providing part 120, a light-receiving part 130, and a processing part 140.

The measurement stage 110 is open upward, and a measurement target MT is located on the measurement stage 100. The measurement stage 110 may control a position, an orientation, etc. of the measurement target MT by a processing part 140 or an externally provided control unit.

The light-providing part 120 provides incident lights IL to the measurement target MT. The light-providing part 120 provides multi-directional incident lights to the measurement target MT from multiple upper directions at which the measurement stage 110 is open.

The multi-directional incident lights indicates incident lights IL according to each direction relative to the measurement target MT, when the incident lights IL are incident from the multiple upper directions of the measurement target MT. The incident direction of the multi-directional incident lights may be represented by an incident angle θ inclined with respect to the normal direction to the measurement target MT. For example, the incident light IL may be incident in all directions above, and the multi-directional incident lights may indicate an incident direction by using an incident angle θ with an oblique angle between 0 and 90 degrees.

The light-providing part 120 includes a plurality of illumination sections 120 a.

The plurality of illumination sections 120 a may be arranged according to various embodiments described below so as to provide the multi-directional incident lights from a plurality of directions onto the measurement target MT.

For example, each of the illumination sections 120 a may include a light source, and provides the light generated from the light source uniformly in each direction to the measurement target MT. Although the illumination sections 120 a are shown as a one-dimensional light source in FIG. 1 since the illumination section 120 a is shown in cross-section, the illumination sections 120 a may actually correspond to a two-dimensional planar light source.

For example, when the incident lights IL generated from the illumination sections 120 a are provided at a point '0' on the measurement target MT, which meets the optical axis of the light-receiving part 130, solid angles of the incident lights IL covered by the size of each illumination section 120 a may be formed to be uniform, and the solid angles may be formed to be substantially the same regardless of which incident light IL and which illumination section 120 a (for example, SA1, SA2, SA3, etc. are the same).

In one embodiment, each of the illumination sections 120 a may include a base substrate (not shown), a plurality of light sources (not shown) formed on the base substrate, and a diffuser (not shown) disposed in front of the light sources to diffuse light generated from the light sources. For example, the light sources may include LEDs, and the light generated from the LEDs may be diffused through the diffuser to provide uniform incident light to the measurement target MT.

The plurality of illumination sections 120 a may be controlled such that the multi-directional incident lights from a plurality of directions are directed to the measurement target MT at the same amount of light. For example, the plurality of illumination sections 120 a may be formed to generate the same amount of light, respectively, for which the plurality of light sources are uniformly disposed in each illumination section 120 a, the plurality of illumination sections 120 a may be formed to have substantially the same size as each other.

Thus, the measurement target MT may be provided with incident light of the same amount of light with respect to the incident direction, i.e., the incident angle θ. The illumination sections 120 a may be driven one by one, for example, in the direction of a thick arrow shown in FIG. 1, in which case the driving of the illumination sections 120 a may be controlled by a processing part 140 or an externally provided control unit or the like.

The light-receiving part 130 obtains the reflection lights RL of the measurement target MT by the multi-directional incident lights illuminated by the light-providing part 120.

In one embodiment, the light-receiving part 130 may include an optical sensor capable of measuring the intensities of reflection lights RL that the multi-directional incident lights are reflected by the measurement target MT to form, and may include a camera such as a CCD or CMOS camera. In addition, the light-receiving part 130 may include a lens disposed in front of the optical sensor or the camera.

In one embodiment, the light-receiving part 130 may receive reflection lights vertically and upwardly reflected from the measurement target MT so as to receive the reflection lights RL of the measurement target MT uniformly with respect to illumination directions of the incident lights IL.

For example, the light-receiving part 130 may be disposed vertically above the measurement target MT as shown in FIG. 1 so as to receive all of the multi-directional incident lights having incident directions of incident angles between 0 and 90 degrees. Alternatively, the light-receiving part 130 may be arranged to receive reflection lights RL reflected vertically upward by employing a suitable light path changing unit, such as a mirror.

The processing part 140 acquires a multi-directional intensity distribution of the single-directional reflection lights reflected by the measurement target MT. The processing part 140 of the illumination system of the present invention may be implemented by, for example, a computer, a computing processor, or the like.

Particularly, the intensity distribution of the reflection lights RL may be expressed in terms of the relationship of the multi-directional incident lights. That is, the intensities of the reflection lights RL may be expressed according to the incident angles θ corresponding to the incident directions of the multi-directional incident lights. For example, the multi-directional incident lights may represent the incident directions thereof as an incident angle between 0° and 90°, and the intensities of the reflection lights RL may be expressed according to the incident angles of the multi-directional incident lights.

The intensity distribution of the reflection lights RL according to the incident angles of the multi-directional incident lights, which is obtained as described above, is a distribution formed by measuring the intensities of "single-directional" reflection lights with respect to "multi-directional" incident lights, which is defined as a first distribution. In addition, another distribution formed by measuring intensities of "multiple-directional" reflection lights with respect to a "single-directional" incident light is considered, which is defined as a second distribution.

However, a relative angle between the "single-directional" reflection lights and a specific incident light among the "multi-directional" incident lights is substantially same as a relative angle between a "single-directional" incident light and a specific reflection light among "multi-directional" reflection lights in which an intensity distribution is formed by measuring intensities of the multi-directional reflection lights. Therefore, in this embodiment, the first distribution of the single-directional reflection lights RL according to the incident angles of the multi-directional incident lights is substantially same as the second distribution of the multi-directional reflection lights reflected by the measurement target MT according to a single-directional incident light.

For example, in the first distribution, as shown in FIG. 1, the incident lights are provided from various directions in the light-providing part forming a dome shape, and the reflected lights are received vertically above by the light-receiving part. In the second distribution, the light-providing part and the light-receiving part may operate in a manner that an incident light is provided vertically downward by the light-providing part arranged vertically above and reflected lights are received by the light-receiving part forming the dome shape.

In the first distribution, a first relative angle is obtained between the single-directional reflected lights with respect to a specific incident light (for example, the incident light IL indicated by the dotted line in FIG. 1) among the multi-directional incident lights. In the second distribution, a second relative angle is obtained between a specific reflection light (for example, corresponding to the direction of the specific incident light in the first distribution) among the multi-directional reflection lights with respect to a single-directional incident light (vertically above the measurement object). Although the incident lights and the reflected lights form opposite optical paths in the first and second distributions, the first relative angle and the second relative angle are substantially equal to each other.

It is well known that an optical path and a ratio between light intensities (i.e., an intensity ratio of reflection light to incident light) are reversible when light reflection corresponds to a linear case, while in contrast changes to physical property of reflecting material may be caused by light in a nonlinear case. Thus, in the present embodiment of the first and second distributions, although optical paths (or light traveling directions) between incident light and reflected light of one distribution are opposite to those of the other distribution, but the optical paths are mutually reversible since they are linear. Thus, the ratios of the light intensities are also reversible. Therefore, the first relative angle of the first distribution is substantially same as the second relative angle of the second distribution.

Accordingly, since the first and second relative angles are substantially same and the optical paths and light intensities are all reversible, the first distribution and the second distribution may be substantially same each other.

In other words, the first distribution of intensities of the reflection lights RL according to the incident angles of the multi-directional incident lights is substantially same as the second distribution of intensities of multiple-directional reflection lights of the measurement target MT according to a single-directional incident light, and thus the second distribution of intensities of multiple-directional reflection lights of the measurement target MT according to a single-directional incident light may be acquired from the first distribution.

Since the measurement target MT may have different second distributions of intensities of multi-directional reflection lights depending on different material, the processing part 140 may determine the material of a specific measurement target MT from a specific second distribution of intensities of multi-directional reflection lights.

Hereinafter, it is described in detail with reference to the drawings how the processing part 140 determines the material of a specific measurement target MT by means of a specific second distribution of intensities of multi-directional reflection lights.

Figure 2:
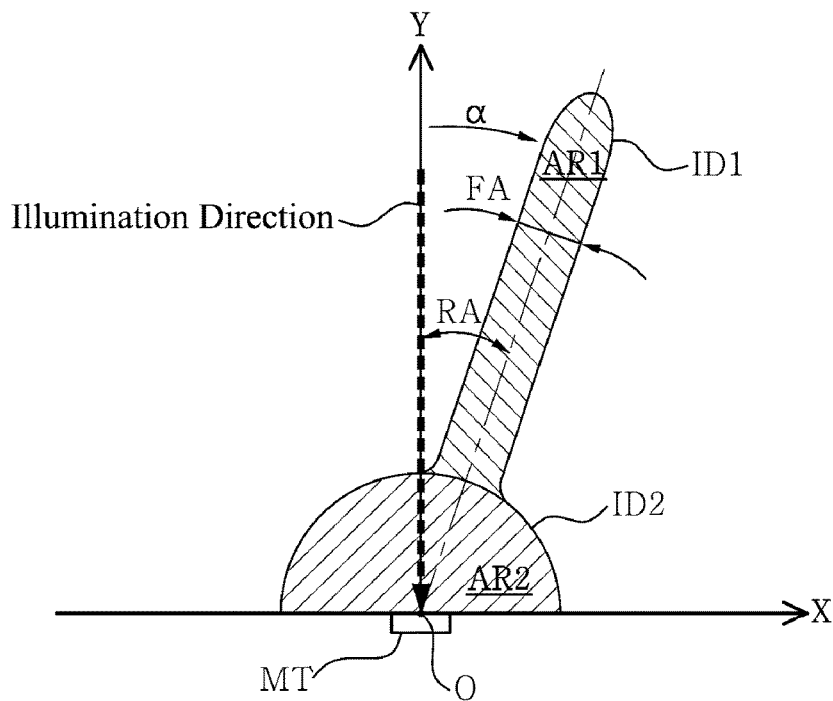
FIGS. 2 and 3 are graphs for explaining the determination of the material of the measurement target in a processing part of the illumination system for recognizing material in FIG. 1.
Figure 3:
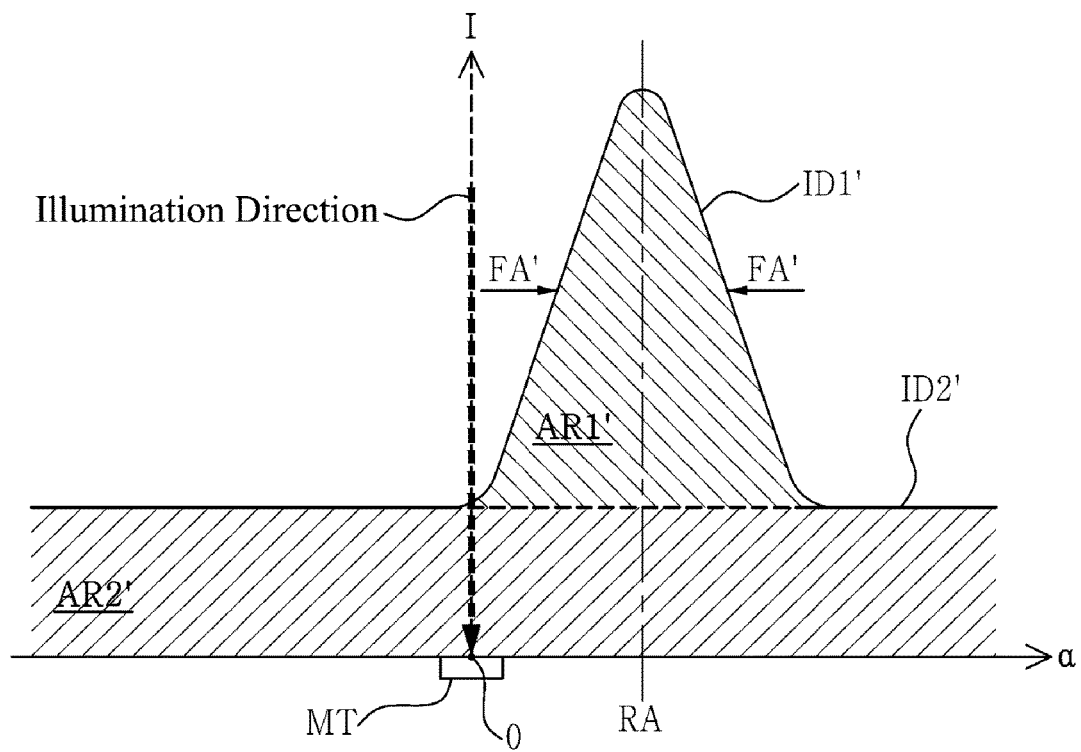

FIGS. 2 and 3 are graphs for explaining the determination of the material of the measurement target in a processing part of the illumination system for recognizing material in FIG. 1.

The graph of FIG. 2 shows the second distribution of intensities of the multi-directional reflection lights reflected by the measurement target MT according to a single-directional incident light, which can be acquired, as explained above in detail, from the reflection lights RL reflected by the measurement target MT according to the multi-directional incident lights. Particularly, the graph of FIG. 2 represents that when a single-directional light is incident onto the origin O, at which the measurement target MT is positioned, substantially parallel to Y-axis, an intensity of a reflection light reflected at a reflection angle α inclined to Y-axis is shown as a distance from the origin O.

The graph of FIG. 3 is a graph in a coordinate system between reflection angle and reflection intensity, which is converted from the graph of FIG. 2. The horizontal axis thereof represents reflection angle θ and the vertical axis thereof represents reflection intensity I.

The processing part 140 may determine the material of the measurement target MT from the second distribution of intensities of the reflection lights, such as the graphs of FIGS. 2 and 3.

In the exemplary embodiment of the present invention, the second distribution of intensities of the multi-directional reflection lights, which may be obtained from the first distribution of intensities of the single-directional reflection lights as described above in detail, may be expressed by a first intensity distribution (ID1 or ID1') of specular reflection lights and a second intensity distribution (ID2 or ID2') of diffuse reflection lights.

The processing part 140 may determine the material of the measurement target MT from the first intensity distribution (ID1 or ID1') and the second intensity distribution (ID2 or ID2'), which form the second distribution of intensities of the reflection lights.

For example, the processing part may determine the material of the measurement target based on at least one parameter among an area (AR1 or AR1') of the first intensity distribution (ID1 or ID1'), an area (AR2 or AR2') of the second intensity distribution (ID2 or ID2'), a total area of the first intensity distribution (ID1 or ID1') and the second intensity distribution (ID2 or ID2'), a reflection angle of the first intensity distribution (ID1 or ID1'), and a spreading angle (FA, FA') of the first intensity distribution (ID1 or ID1').

The area (AR1 or AR1') of the first intensity distribution (ID1 or ID1') is a parameter representing an area occupied by the first intensity distribution (ID1 or ID1') generally having an elongated nipple shape (see FIG. 2) or a triangular shape (see FIG. 3), from which a specular reflectance of the measurement target MT may be obtained.

The area (AR2 or AR2') of the second intensity distribution (ID2 or ID2') is a parameter representing an area occupied by the second intensity distribution (ID2 or ID2') generally having a semicircular shape (see FIG. 2) or a rectangular shape (see FIG. 3), from which a diffuse reflectance of the measurement target MT may be obtained.

The total area of the first intensity distribution (ID1 or ID1') and the second intensity distribution (ID2 or ID2') is a parameter representing a total area occupied by the first intensity distribution (ID1 or ID1') and the second intensity distribution (ID2 or ID2'), from which a total reflectance of the measurement target MT may be obtained.

The reflection angle (RA) of the first intensity distribution (ID1 or ID1') is a parameter representing an angle at which a symmetrical axis of the first intensity distribution (ID1) is inclined with respect to the single-directional incident light that is incident substantially parallel to Y-axis, from which a slope of the surface of the measurement target MT may be obtained.

The spreading angle (FA) of the first intensity distribution (ID1 or ID1') is a parameter representing a width of the elongated nipple shape (see FIG. 2) or a half width of the triangular shape (see FIG. 3), from which a glittering degree of the measurement target MT may be obtained.

The processing part 140 may determine the material of the measurement target MT based on at least one parameter of the above mentioned parameters.

In one example, in case that the total reflectance of the measurement target MT obtained from the total area of the first intensity distribution (ID1 or ID1') and the second intensity distribution (ID2, ID2') is greater than about 40%, and the area (AR2 or AR2') of the second intensity distribution (ID2 or ID2') is very small and thus the diffuse reflectance of the measurement target MT smaller than a reference value, the measurement target MT may be determined to be metal material.

In another example, in case that the diffuse reflectance of the measurement target MT obtained from the area (AR2 or AR2') of the second intensity distribution (ID2 or ID2') is greater than about 40%, the spreading angle (FA or FA') of the first intensity distribution (ID1 or ID1') indicating the glittering degree of the measurement target MT is greater than about 40°, and the total reflectance of the measurement target MT obtained from the total area of the first intensity distribution (ID1 or ID1') and the second intensity distribution (ID2, ID2') is greater than about 50%, the measurement target MT may be determined to be paper material.

For the above determination of material, the reference data is preliminarily obtained through experiments on various materials, and thereafter an actually desired measurement target is measured and compared with the reference data to thereby determine the material.

Thus, the processing part 140 may simply and easily determine the material of the measurement target MT using the parameters as described above.

Hereinafter, various embodiments of the illumination system for recognizing material will be described in more detail with reference to the drawings.

Figure 4:
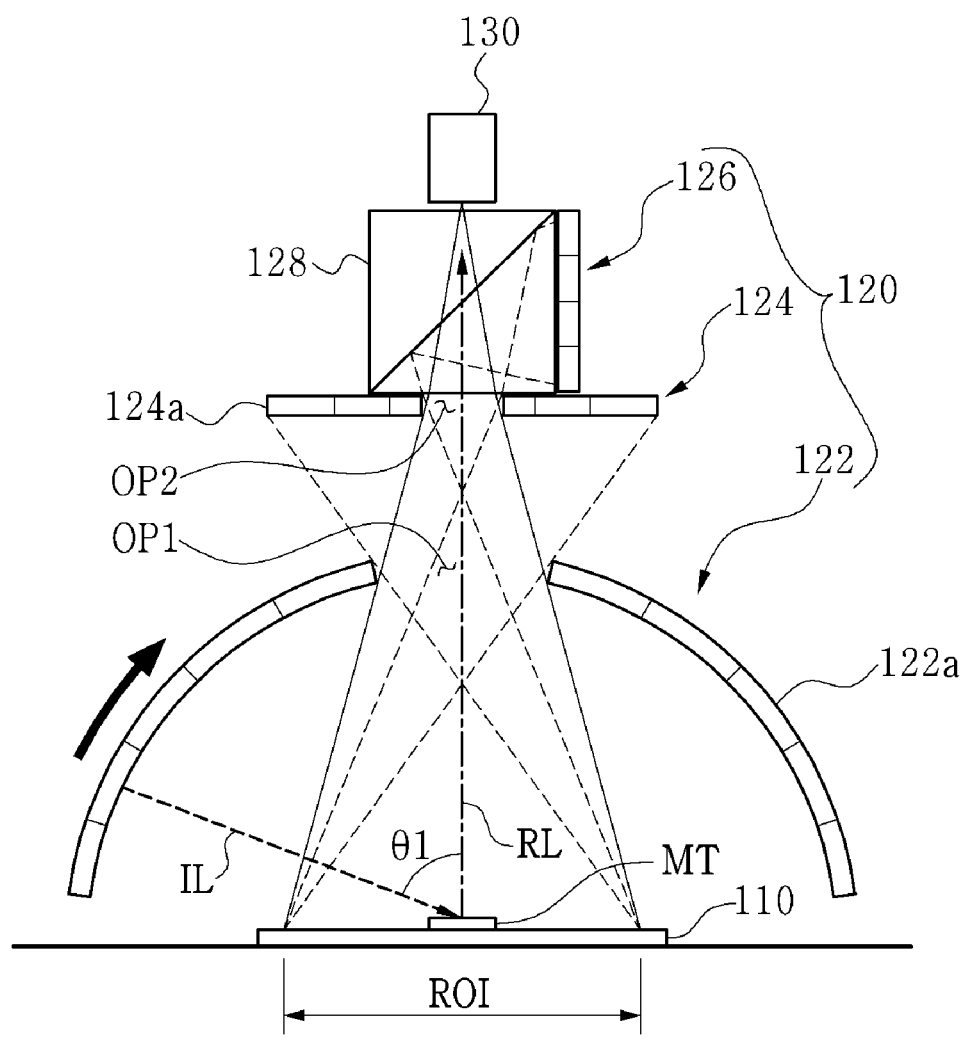
FIG. 4 is a front view showing an embodiment of the illumination system for recognizing material in FIG. 1.
Figure 5:
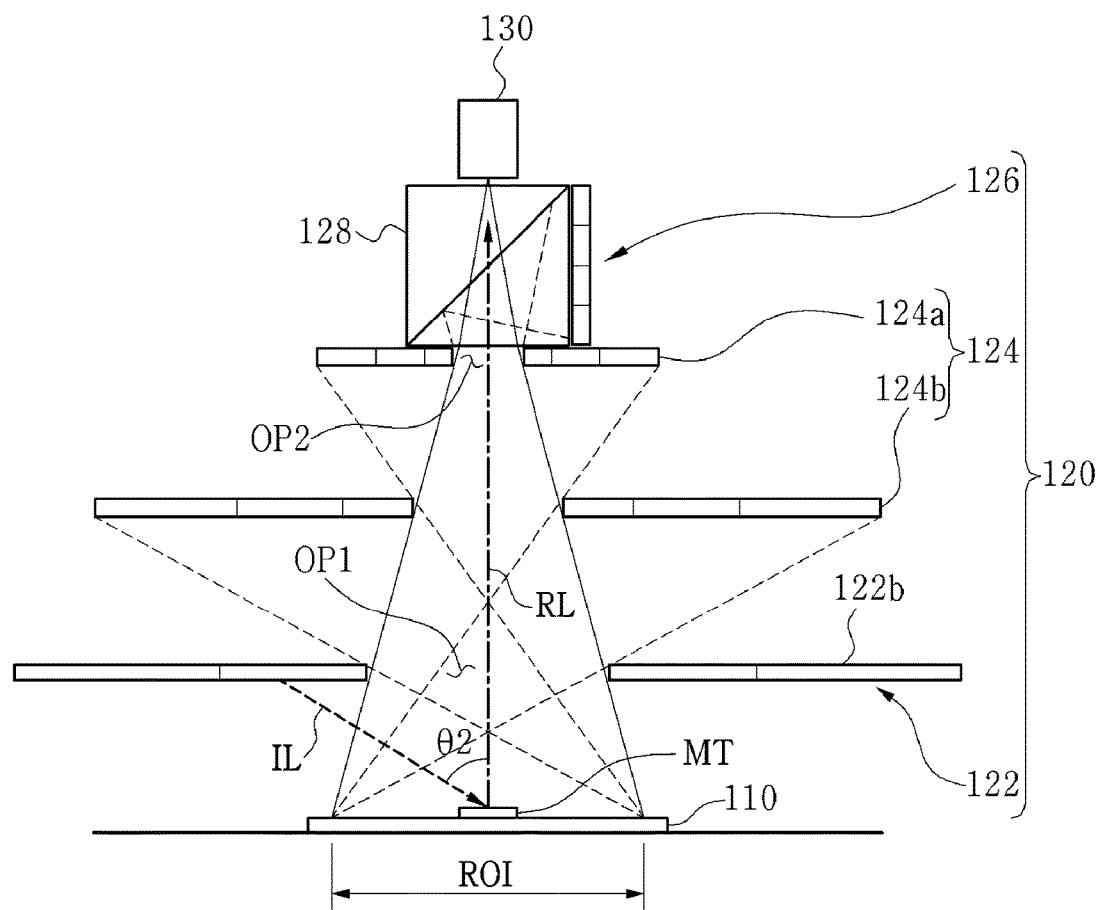
FIG. 5 is a front view showing another embodiment of the illumination system for recognizing material in FIG. 1.
Figure 6:
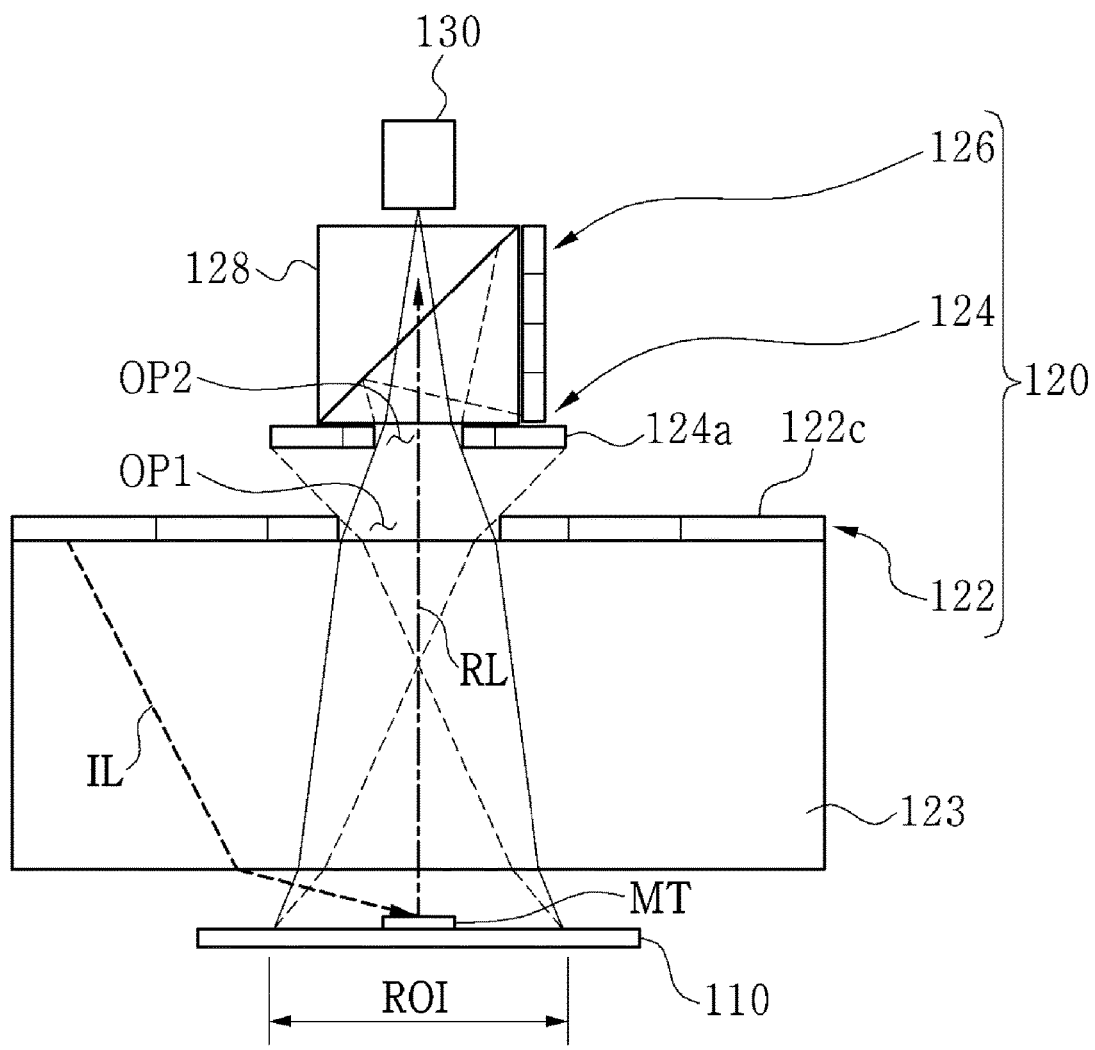
FIG. 6 is a front view showing still another embodiment of the illumination system for recognizing material in FIG. 1.

FIG. 4 is a front view showing an embodiment of the illumination system for recognizing material in FIG. 1. FIG. 5 is a front view showing another embodiment of the illumination system for recognizing material in FIG. 1. FIG. 6 is a front view showing still another embodiment of the illumination system for recognizing material in FIG. 1.

Referring to FIGS. 1, 4 to 6, the light-providing part 120 of the illumination system 100 may include a plurality of illumination sections 122 covering at least a portion of the multiple upper directions at which the measurement stage is open.

In one embodiment, the first illumination sections 122 may form at least a portion of a dome shape 122 a, as shown in FIG. 4.

The first illumination sections 122 may be arranged to form at least a portion of the dome shape so as to provide the multi-directional incident lights from a plurality of directions onto the measurement target MT, and may be arranged as shown in FIG. 4 to form a circular shape having an opening at the center when viewed from the upper direction, and a semicircular shape having an opening at the top when viewed from the front direction.

For example, each of the first illumination sections 122 may be formed such that the multi-directional incident lights are uniformly provided onto the measurement target MT. That is, each of the first illumination sections 122 may be formed to cover substantially the same solid angle regardless of the direction with respect to the measurement target MT, i.e., the incident angle θ1. To this end, each of the first illumination sections 122 may be formed to generate substantially the same amount of light with substantially the same size having substantially the same curvature, so that the multi-directional incident lights may be incident onto the measurement target MT, with covering substantially the same solid angle for each direction.

In another embodiment, the first illumination sections 122 may form at least a portion of a plate shape 122 b, as shown in FIG. 5. For example, the plate shape 122 b may have a circular or polygonal shape.

The first illumination sections 122 may be arranged to form at least a portion of the plate shape to provide the multi-directional incident lights from the plurality of directions onto the measurement target MT, and arranged to form a donut shape, i.e., a circular plate shape, the center of which is open when viewed from an upper direction.

For example, each of the first illumination sections 122 may be formed such that the multi-directional incident lights are uniformly provided onto the measurement target MT. That is, each of the first illumination sections 122 may be formed to cover substantially the same solid angle regardless of the direction with respect to the measurement target MT, i.e., the incident angle θ2. Particularly, when the incident lights IL generated from the first illumination sections 122 is incident on a point (corresponding to the origin O in FIG. 2) on the measurement target MT, which meets the optical axis of the light-receiving part 130, the solid angles of the incident lights IL covered by the sizes of first illumination sections 122 may be formed to be uniform. To this end, sizes of the first illumination sections 122 may get smaller from the periphery toward the center of the measurement target MT. In other words, the sizes of the first illumination sections 122 vary in such a manner that sections closer to the center of the measurement target are smaller than sections farther from the center of the measurement target so that solid angles of the incident lights covered by the first illumination sections are uniform.

In still another embodiment, the first illumination sections 122 may form at least a portion of a plate shape 122 c, as shown in FIG. 6. For example, the plate shape 122 c may be circular shape or a polygonal shape. Herein, a refractive medium unit 123 may be disposed under the first illumination sections 122. The refractive medium unit 123 refracts the light generated from the first illumination sections 122 to have a larger incident angle with respect to the measurement target MT.

The first illumination sections 122 shown in FIG. 6 are similar to the first illumination sections 122 shown in FIG. 5 in that the first illumination sections 122 may be disposed to form at least a portion of a plate shape so as to provide the multi-directional incident lights from the multiple directions, but may obtain substantially the same incident lights IL with a smaller quantity of illumination sections in comparison with the case of FIG. 5.

Referring again to FIGS. 4 to 6, in one embodiment, a shape formed by the first illumination sections 122 may be formed with a first opening portion OP1 at least partially open. The light-receiving part 130 may be arranged to receive reflection lights RL reflected from the measurement target MT through the first opening portion OP1.

In one embodiment, the light-providing part 120 may further include at least one second illumination section 124.

The second illumination section 124 provides incident light to the measurement target MT through the first opening portion OP1 and is disposed so as to acquire the reflection lights RL corresponding to a region of interest (ROI) including at least a portion of the measurement target MT.

A portion of the first illumination sections 122 may be removed and the light-receiving part 130 may be disposed at the removed location so as to receive the reflection lights RL reflected by the measurement target MT. In this case, the light-receiving part 130 may be spaced from the measurement target MT by a specific distance in order to receive the reflection lights RL corresponding to the ROI including all or portion of the measurement target MT. Thus, depending on the size of the ROI, the light-receiving part 130 may be required to be sufficiently spaced from the measurement target MT, so that positions of the first illumination sections 122 may also be required to be correspondingly spaced from the measurement target MT, which may incur a problem that the illumination system 100 may become excessively large.

Thus, the shape formed by the first illumination sections 122 may be formed with a first opening portion OP1 at least partially open, and the light-receiving part 130 may be arranged to acquire the reflection lights RL via the first opening portion OP1, specifically acquire the reflection lights RL corresponding to a region including the ROI. Further, the second illumination section 124 may provide incident light to the measurement object MT through the first opening portion OP1 to compensate for partial absence of multi-directional incident lights due to the first opening portion OP1.

For example, the second illumination section 124 may form at least a portion of a plate shape. The plate shape may have a circular or polygonal shape, as previously described in the first illumination section 122 of FIG. 5, and may include, for example, a circular plate shape with an opening at the center when viewed from the upper direction, i.e., a donut shape.

The second illumination section 124 may include a plurality of layers 124a and 124 b forming at least a portion of the plate shape, as shown in FIG. 5. It may be preferable to configure the second illumination section 124 as a plurality of layers when the size of the ROI is large or the illumination system 100 is desired to be compact.

In one embodiment, a shape formed by the at least one second illumination section 124 may be formed with a second opening portion OP2, and the light-receiving part 130 may be arranged to acquire the reflection lights RL reflected by the measurement target MT via the second opening portion OP2.

That is, when the light-receiving part 130 receives reflection lights RL reflected by the measurement target MT, the second opening portion OP2 may be formed in order that the reflection lights RL may travel toward the light-receiving part 130.

In this case, since the light-providing part 120 may not provide the incident light to the measurement target MT in the position where the second opening portion OP2 is formed, in one embodiment, the illuminating unit 120 may further include a third illuminating section 126 and a beam splitting unit 128.

The third illumination section 126 provides incident light to the measurement target MT through the second opening portion OP2 and the beam splitting unit 128 transmits the reflection lights RL to the light-receiving part 130 and reflects the incident light generated from the third illumination section 126 to provide the measurement target MT with the reflected incident light as an optical axis substantially the same as an optical axis of the light-receiving part 130.

Thus, the incident light IL may be provided to the measurement target MT in substantially the same optical axis direction as the optical axis of the light-receiving part 130.

In the illumination system 100 (referring back to FIG. 1), when acquiring the second distribution of intensities of the multi-directional reflection lights RL of the measurement target MT according to a single-directional incident light from the first distribution of intensities of the single-directional reflection lights RL of the measurement target MT according to the multi-directional incident lights, the second distribution may be obtained at any one point of the measurement target MT, for example, at one pixel. Therefore, the acquisition of the second distribution of the reflection lights may be hardly affected by the posture of the measurement target MT.

However, in order to minimize the influence of the posture of the measurement target MT, the illumination system 100 may further include a posture adjusting unit (not shown) adjusting the posture of the measurement target MT, so as to maintain the posture of the measurement target MT constant with respect to the incident directions of the multi-directional incident lights.

The posture adjusting unit may receive the measurement target MT to fix the posture of the measurement target MT, and may be controlled by the processing part 140 or an externally provided control unit.

Figure 7:
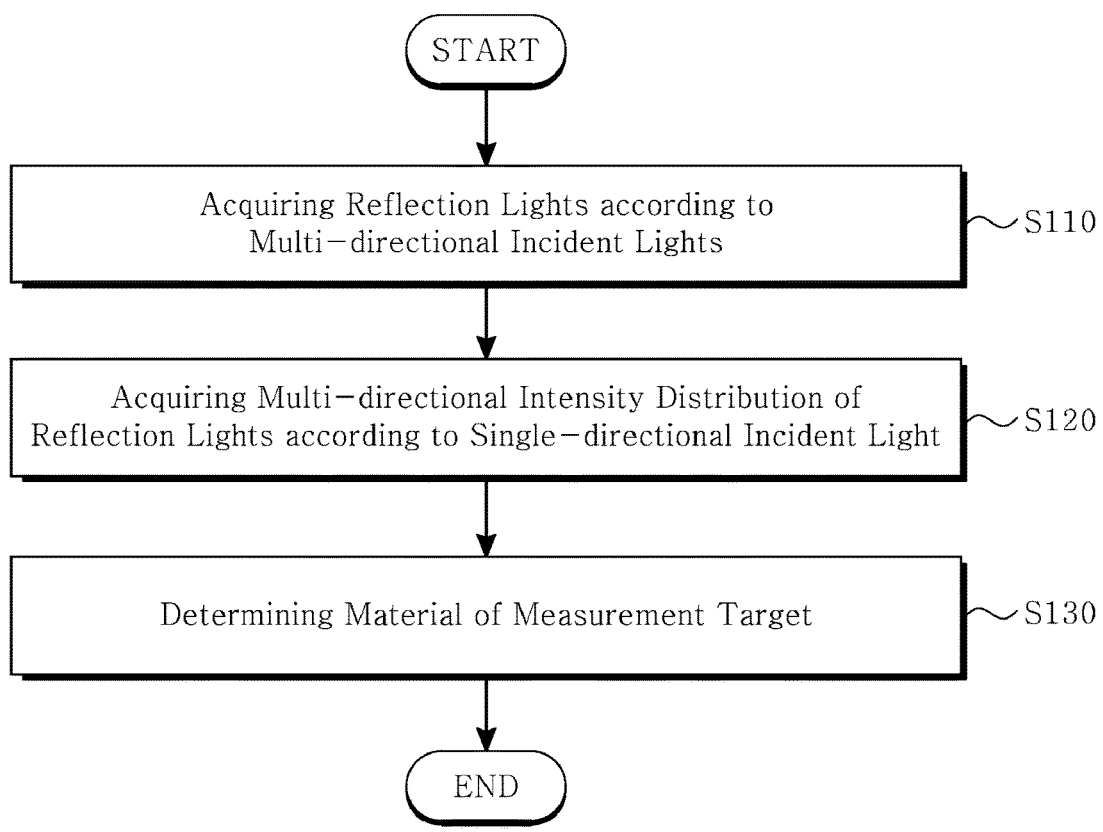
FIG. 7 is a flowchart illustrating a method of recognizing material using an illumination system according to an exemplary embodiment of the present invention.

FIG. 7 is a flowchart illustrating a method of recognizing material using an illumination system according to an exemplary embodiment of the present invention.

Referring to FIGS. 1 and 7, a method of recognizing material according to an exemplary embodiment of the present invention may use the illumination system 100 described above.

The method of the present invention includes a step that single-directional reflection lights according to multi-directional incident lights are obtained (S110).

Particularly, the single-directional reflection lights RL of the measurement target MT, according to the multi-directional incident lights that are provided from multiple directions towards the measurement target MT, are acquired. As a result, acquired is a first distribution of intensities of the single-directional reflection lights.

By use of the first distribution, a second distribution of intensities of multi-directional reflection lights according to a single-directional incident light is acquired (S120).

Particularly, the second distribution of intensities of the multi-directional reflection lights reflected by the measurement target MT according to the single-directional incident light is acquired from the single-directional reflection lights RL of the measurement target MT according to the multi-directional incident lights.

Thereafter, the material of the measurement target MT is determined from the second distribution (S130).

Particularly, the material of the measurement target MT is determined from first and second intensity distributions of the second distribution of the reflection lights.

As described above, the material of the measurement target MT may be determined from a first intensity distribution of specular reflection lights and a second intensity distribution of diffuse reflection lights, and may be determined based on at least one parameter among an area of the first intensity distribution, an area of the second intensity distribution, a total area of the first intensity distribution and the second intensity distribution, a reflection angle of the first intensity distribution, and a spreading angle of the first intensity distribution.

In addition, the more detailed process is substantially the same as the method described in FIG. 1 to FIG. 6. Thus, redundant detailed description will be omitted.

According to the illumination system for recognizing material and the method of recognizing material using the illumination system, multi-directional incident lights from a plurality of directions are provided to a measurement target to obtain reflection lights in a single direction, from which a distribution of intensities of multi-directional reflection lights of the measurement target according to a single-directional incident light is acquired, to determine the material of the measurement target from the distribution of the multi-directional reflection lights, thereby easily and accurately recognizing the material of the measurement target at a low cost in comparison with conventional systems.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An illumination system for recognizing material comprising:
    a measurement stage that is upwardly open and on which a measurement target is located;
    a light-providing part including a plurality of illumination sections providing multi-directional incident lights to the measurement target, the multi-directional incident lights having incident directions of incident angles, respectively;
    a light-receiving part receiving single-directional reflection lights reflected by the measurement target according to the multi-directional incident lights provided by the light-providing part; and
    a processing part that performs steps of:
        acquiring a first distribution of intensities the single-directional reflection lights with respect to the multi-directional incident lights;
        acquiring, from the first distribution, a second distribution of intensities of multi-directional reflections lights with respect to a single-directional incident light, wherein the multi-directional reflection lights of the second distribution have optical paths opposite to optical paths of the multi-directional incident lights of the first distribution, and the single-directional incident light of the second distribution has an optical path opposite to an optical path of the single-directional reflection lights of the first distribution; and
        determining material of the measurement target based on parameters of the second distribution,
    wherein the parameters are acquired from a first intensity distribution of specular reflection lights and a second intensity distribution of diffuse reflection lights, the first and second intensity distributions forming the second distribution, and
    wherein the parameters include at least one of an area or the first intensity distribution, an area of the second intensity distribution, a total area of the first and second intensity distributions, a reflection angle of the first intensity distribution, and a spreading angle of the first intensity distribution.

2. The illumination system of claim 1, wherein the light-providing part includes a plurality of first illumination sections covering at least a portion of multiple upper directions at which the measurement stage is open,
    wherein the first illumination sections form at least a portion of a dome shape.

3. The illumination system of claim 2, wherein each of the first illumination sections includes:
    a base substrate;
    a plurality of light sources formed on the base substrate; and
    a diffuser disposed in front of the light sources to diffuse light generated from the light sources.

4. The illumination system of claim 1, wherein the light-providing part includes a plurality of first illumination sections covering at least a portion of multiple upper directions at which the measurement stage is open,
    wherein the first illumination sections form at least a portion of a plate shape, and
    wherein the multi-directional incident lights generated from the first illumination sections are provided at a point on the measurement target, the point meets an optical axis of the light-receiving part, and sizes of the first illumination sections vary in such a manner that sections closer to a center of the measurement target are smaller than sections farther from the center of the measurement target so that solid angles of the incident lights covered by the first illumination sections are uniform.

5. The illumination system of claim 4, wherein the light-providing part further includes a refractive medium unit disposed below the first illumination sections to refract light generated from the first illumination sections so as to have a larger incident angle with respect to the measurement target.

6. The illumination system of claim 1, wherein the light-providing part includes a plurality of first illumination sections covering at least a portion of multiple upper directions at which the measurement stage is open,
    wherein the first illumination sections form at least a portion of a dome shape or a plate shape,
    a first opening portion is formed through a shape of the first illumination sections, and
    the light-receiving part is arranged so as to receive the reflection light reflected by the measurement target through the first opening portion.

7. The illumination system of claim 6, wherein the light-providing part further includes at least one second illumination section that provides incident light to the measurement target through the first opening portion, and is configured to acquire the reflection light corresponding to a region of interest (ROI) including at least a portion of the measurement target.

8. The illumination system of claim 7, wherein the at least one second illumination section is formed as a plurality of layers forming at least a portion of a plate shape.

9. The illumination system of claim 7, wherein a second opening portion is formed through a shape of the at least one second illumination section, and
    the light-receiving part is arranged so as to receive the reflection light reflected by the measurement target through the second opening portion.

10. The illumination system of claim 6, wherein the light providing part further includes:
    a subsidiary illumination section providing incident light to the measurement target through the first opening portion; and
    a beam splitting unit that transmits the reflection lights to the light-receiving part and reflects the incident light generated from the subsidiary illumination section to provide the measurement target with the reflected incident light as an optical axis substantially the same as an optical axis of the light-receiving part.

11. The illumination system of claim 1, wherein the light-receiving part receives the single-directional reflection lights vertically and upwardly reflected from the measurement target, the single-directional reflection lights being uniformly received with respect to illumination directions of the incident lights.

12. The illumination system of claim 1, wherein a value of each of the parameters is obtained on a coordinate system between reflection angle and reflection intensity.

13. A method of recognizing material using an illumination system, comprising:
   providing, by a light-providing device, multi-directional incident lights toward a measurement target, the multi-directional incident lights having incident directions of incident angles, respectively;
   receiving, by a light-receiving device, single-directional reflection lights reflected from the measurement target;
   acquiring, by a processor, a first distribution of intensities of the single-directional reflection lights with respect to the multi-directional incident lights;
   acquiring from the first distribution, by the processor, a second distribution of intensities of the multi-directional reflection lights with respect to a single-directional incident light,
   wherein the multi-directional reflection lights of the second distribution have optical paths opposite to optical paths of the multi-directional incident lights of the first distribution, and the single-directional incident light of the second distribution has an optical path opposite to an optical path of the single-directional reflection lights of the first distribution; and
   determining, by the processor, material of the measurement target based on parameters of the second distribution
   wherein the parameters are acquired front a first intensity distribution of specular reflection lights and a second intensify distribution of diffuse reflection lights, the first and second intensity distributions form the second distribution, and
   wherein the parameters include at least one of an area of the first intensity distribution, an area of the second intensity distribution, a total area of the first and second intensity distributions, a reflection angle of the first intensity distribution, and a spreading angle of the first intensity distribution.

14. A computer readable non-transitory recording medium recording a program embodying the method of claim 13.

* * * * *